United States Patent
Amino et al.

(10) Patent No.: US 7,115,296 B2
(45) Date of Patent: Oct. 3, 2006

(54) N-ALKYLASPARTYL AMIDE DERIVATIVE AND SWEETENING AGENT

(75) Inventors: Yusuke Amino, Kawasaki (JP); Kazuko Yuzawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 272 days.

(21) Appl. No.: 10/636,770

(22) Filed: Aug. 8, 2003

(65) Prior Publication Data

US 2004/0071851 A1 Apr. 15, 2004

Related U.S. Application Data

(63) Continuation of application No. PCT/JP02/00419, filed on Jan. 22, 2002.

(30) Foreign Application Priority Data

Feb. 8, 2001 (JP) ............................. 2001-032175

(51) Int. Cl.
A23L 1/236 (2006.01)

(52) U.S. Cl. .................. 426/548; 426/590; 560/40; 560/41

(58) Field of Classification Search ............... 426/548, 426/590, 658; 558/412; 560/40, 41; 562/450
See application file for complete search history.

(56) References Cited

U.S. PATENT DOCUMENTS

| | | | |
|---|---|---|---|
| 4,423,029 A | 12/1983 | Rizzi | |
| 5,480,668 A | 1/1996 | Nofre et al. | |
| 5,777,159 A | 7/1998 | Nofre et al. | |
| 5,997,933 A | 12/1999 | Nofre et al. | |
| 6,010,733 A | 1/2000 | Takemoto et al. | |
| 6,548,096 B1 * | 4/2003 | Amino et al. | 426/548 |
| 6,630,191 B1 * | 10/2003 | Amino et al. | 426/548 |
| 6,649,784 B1 * | 11/2003 | Amino et al. | 560/41 |
| 6,794,531 B1 * | 9/2004 | Nagashima et al. | 560/40 |
| 6,899,912 B1 * | 5/2005 | Amino et al. | 426/548 |
| 6,939,987 B1 * | 9/2005 | Amino et al. | 560/40 |

FOREIGN PATENT DOCUMENTS

| | | |
|---|---|---|
| EP | 0 203 540 | 12/1986 |
| FR | 2 719 592 | 11/1995 |
| WO | 94/11391 | 5/1994 |
| WO | 97/29122 | 8/1997 |
| WO | WO 00/17230 A1 | 3/2000 |

OTHER PUBLICATIONS

Robert H. Mazur et al, "Structure-Taste Relationships of Aspartic Acid Amides", *Journal of Medicinal Chemistry*, 1970, pp. 1217-1221, vol. 13, No. 6.

Yoshifumi Yuasa et al, "The Sweetness and Stereochemistry of L-Aspartyl-Fenchylaminoalcohol Derivatives", *Tetrahedron Letters*, 1994, pp. 6891-6894, vol. 35, No. 37.

Ahmed F. Abdel-Magid et al, "Reductive Amination of Aldehydes and Ketones By Using Sodium Triacetoxyborohydride", *Tetrahedron Letters*, 1990, pp. 5595-5598, vol. 31, No. 39.

Mark W. Holladay et al, "Synthesis of Hydroxyethylene and Ketomethylene Dipetide Isosteres", *Tetrahedron Letters*, 1983, pp. 4401-4404, vol. 24, No. 41.

Manfred T. Reetz et al, "Stereoselective Synthesis of β-Amino Alcohols from Optically Active α-Amino Acids", *Angew. Chem. Int. Ed. Engl.*, 1987, pp. 1141-1143, vol. 26, No. 11.

M.T. Reetz et al, "Non-Racemiping Synthesis and Stereoselective Reduction of Chiral α-Amino Ketones", *Tetrahedron; Asymmetry*, 1990, pp. 375-378, vol. 1, No. 6.

* cited by examiner

*Primary Examiner*—Leslie Wong
(74) *Attorney, Agent, or Firm*—Oblon, Spivak, McClelland, Maier & Neustadt, P.C.

(57) ABSTRACT

The present invention relates to a novel N-alkylaspartyl amide derivative, a salt form thereof, a sweetening agent containing the same and a sweetened food or drink containing the N-alkylaspartyl amide derivative as an effective ingredient.

24 Claims, No Drawings

N-ALKYLASPARTYL AMIDE DERIVATIVE AND SWEETENING AGENT

CROSS-REFERENCE TO RELATED APPLICATIONS

The present application is a continuation application of PCT International Application No. PCT/JP02/00419, filed on Jan. 22, 2002, which is hereby incorporated by reference in its entirety. In addition, the present application claims priority to Japanese Patent Application No. 2001-032175, filed on Feb. 8, 2001, which is hereby incorporated by reference in its entirety.

BACKGROUND OF THE INVENTION

1. Field of the Invention

The present invention relates to a novel N-alkylaspartyl amide derivative, a salt form thereof, a sweetening agent containing the same and a sweetened food or drink containing the N-alkylaspartyl amide derivative as an effective ingredient.

2. Discussion of the Background

With the significant societal improvements in eating habits in recent years, fatness resulting from excessive sugar intake and diseases accompanied by fatness has come under closer scrutiny. Accordingly, development of a low-calorie sweetener (sweetening agent) to replace sugar has been in increased demand. At present, aspartame has been employed owing to its excellent safety record and quality of sweetness. However, aspartame is somewhat problematic with respect to stability.

One approach to improve stability and enhance sweetening potency of aspartame is the creation of an aspartyl amide derivative by condensation of an aspartic acid and a β-aminoalcohol. The resulting product has no ester linkage. These compounds and derivatives are described in patents, such as U.S. Pat. No. 4,423,029 and EP 0203540A1 Publication, and in technical literature, such as J. Med. Chem., 13, 1217 (1970) and Tetrahedron Letters, 35, 6891 (1994).

An alternative approach is described in the International Patent Publication WO 94/11391, which reports that derivatives in which an alkyl group is introduced on a nitrogen atom of aspartic acid constituting the aspartame markedly improve (enhance) the ratio of the sweetening potency and have a slightly improved stability. Of the compounds set forth in this publication, N-[N-(3,3-dimethylbutyl)-L-α-aspartyl]-L-phenylalanine 1-methyl ester, in which a 3,3-dimethylbutyl group has been employed as an alkyl group has been found to be the best. The sweetening potency of this compound is reported to be 10000 times that of sucrose. However, the sweetening potency of the other derivatives described in the foregoing publication do not exceed 2500 times that of sucrose.

A substituent group having a sweetness-enhancing effect for the aspartame equal to that of the 3,3-dimethylbutyl group therefor, has not been found. Further, examples of the derivatives in which a 3,3-dimethylbutyl group is introduced on a nitrogen atom of aspartic acid constituting an aspartyl dipeptide ester or an aspartyl dipeptide amide in place of the aspartame, are described in the FR 2719592 Publication and the International Patent Publication WO 97/29122. However, a critical need still remains to develop a method which comprises introducing a substituent group (particularly one other than the 3,3-dimethylbutyl group) on a nitrogen atom of aspartic acid constituting an aspartyl amide derivative in place of the aspartame, to obtain a derivative having a sweetening potency equal to or more than that of the N-[N-(3,3-dimethylbutyl)-L-α-aspartyl]-L-phenylalanine 1-methyl ester. Moreover, a critical need exists to develop a low-calorie sweetening agent having a superior sweetening potency compared to sucrose and/or aspartame.

SUMMARY OF THE INVENTION

It is an object of the present invention to provide a novel N-alkylaspartyl amide derivative having excellent stability and safety. The present invention also seeks to provide a novel N-alkylaspartyl amide derivative further possessing a sweetening potency equivalent or superior to that of the above-described N-[N-(3,3-dimethylbutyl)-L-α-aspartyl]-L-phenylalanine 1-methyl ester. Further, the present invention also seeks to provide a low-calorie sweetening agent and a food and/or drink comprising the derivative as an effective component (ingredient).

To achieve the above-mentioned objectives, the present inventors have synthesized N-alkylaspartyl amide derivatives in which a variety of alkyl groups with substituent group(s) (substituted alkyl groups) have been introduced on a nitrogen atom of an aspartic acid, through a reductive alkylation reaction, using a variety of aldehydes and ketones. The stability and the sweetening potency of these derivatives were subsequently assessed. As for the stability, the present inventors have discovered that most of the compounds (derivatives) have a stability of 4 times or more that of the aspartame, in the acidic aqueous solution at a pH value of 3. Also, with respect to the sweetening potency, it has been discovered that the derivatives of the present invention have a sweetening potency equivalent or superior to that of the above-described N-[N-(3,3-dimethylbutyl)-L-α-aspartyl]-L-phenylalanine 1-methyl ester. As such, these derivatives can be easily used for sweetening agents or in foods and drinks.

Therefore, the present invention provides N-alkylaspartyl amide derivatives represented by the following general formula (1), a salt form thereof, a sweetening agent (sweetener) and sweetened products such as a food and drink (food and/or drink) and the like comprising the derivative.

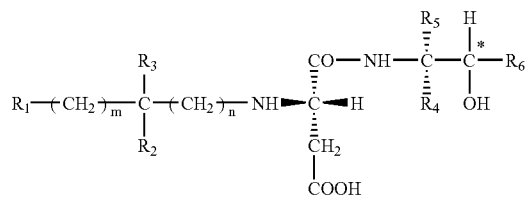
(1)

In formula (1), $R_1$ denotes any one of a hydroxyl group (OH), an alkoxy group having 1 to 4 carbon atoms (e.g., $OCH_3$, $OCH_2CH_3$), an alkoxycarbonyl group having 2 to 5 carbon atoms, and a phenyl or a substituted phenyl (phenyl having substituent group(s)) group represented by the following general formula (2), and

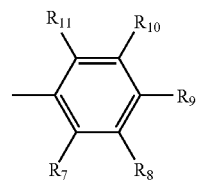
(2)

Where, in the above formula (2), $R_7$, $R_8$, $R_9$, $R_{10}$ and $R_{11}$ are reciprocally independent from each other and each denotes a substituent group selected from a hydrogen atom (—H), a hydroxyl group, an alkoxy group having 1 to 3 carbon atoms, and an alkyl group having 1 to 3 carbon atoms (e.g., $CH_3$, $CH_2CH_3$), wherein $R_7$ and $R_8$, or $R_8$ and $R_9$ may be combined together to form a methylene dioxy group ($OCH_2O$).

In formula (1), $R_2$ and $R_3$ are reciprocally independent from each other and each denotes a substituent group selected from a hydrogen atom and an alkyl group having 1 to 4 carbon atoms, or $R_2$ and $R_3$ are combined together to form an alkylene group having 2 to 5 carbon atoms (e.g., $CH_2CH_2$, $CH_2CH_2CH_2$). In formula (1), m and n are reciprocally independent from each other and each denotes a numerical value selected from 0, 1, 2, 3 and 4. C* indicates any steric configuration. Therefore, there is no particular limitations on the steric configuration at this position and any one configuration of (R), (S) and (RS) may be given thereto. In formula (1), q denotes 0 or 1.

$R_4$ and $R_5$, in formula (1) are reciprocally independent from each other and each denotes a substituent group selected from a hydrogen atom, an alkyl group having 1 to 6 carbon atoms, an alkoxyalkyl group having 2 to 7 carbon atoms, a hydroxyalkyl group having 1 to 6 carbon atoms, a phenyl group and a 2-furyl group, or $R_4$ and $R_5$ can be combined together to form an alkylene group having 2 to 5 carbon atoms. R6, in formula (1), denotes an alkyl group having 1 to 12 carbon atoms, a substituent group represented by the following general formula (3) or a substituent group represented by general formula (4), below:

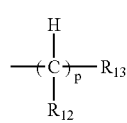
(3)

Where, in formula (3), $R_{12}$ denotes a substituent group selected from a hydrogen atom and an alkyl group having 1 to 4 carbon atoms, and $R_{13}$ denotes a carbocyclic compound residue group which contains three (3) to twelve (12)-membered ring(s), has substituent group(s) or no substituent group, and are saturated or unsaturated. In other words, $R_{13}$ is a carbocyclic compound (alicyclic compound) residue group containing three (3) to twelve (12)-membered ring(s), and with respect to the carbon-carbon bindings constituting the ring (s), may include any one of the residue group wherein all the carbon-carbon bindings constituting the compound are saturated (cycloalkyl group and the like), the residue group wherein at least one of the carbon-carbon bindings thereof is unsaturated (carbon-carbon double bond; cycloalkenyl group and the like, carbon-carbon triple bond; cycloalkynyl group and the like) and the like. In addition, on the carbon atom(s) constituting the ring(s) described above, the residue group may have at least one of the alkyl group(s) having 1 to 5 carbon atoms and/or other substituent group(s). In this case, further at least one carbon atom constituting said ring and the alkyl group(s) and/or other substituent group(s) described above may be combined to constitute an another ring and form a bicyclo alkyl group, a bicyclo alkenyl group, a tricyclo alkyl group or the like. Further, in formula (3) above, p denotes 0 or 1.

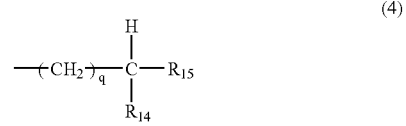
(4)

Where in formula (4), $R_{14}$ and $R_{15}$ are reciprocally independent from each other and each denotes a substituent group selected from a phenyl group, a hydrogen atom, a cycloalkyl group having 3 to 4 carbon atoms, an alkyl group having 1 to 6 carbon atoms, an alkoxyalkyl group having 2 to 7 carbon atoms and a 2- or 3-thienyl group, wherein said phenyl group may have at least one kind of the substituent groups selected from hydroxyl group(s), alkoxy group(s) having 1 to 3 carbon atoms, alkyl group (s) having 1 to 3 carbon atoms and methylene dioxy group(s).

Another object of the present invention is to provide specific high potency and stability derivatives and salt forms thereof, which may be used in a food and drink (food and/or drink).

Further, as an another object, the present invention also provides a sweetening agent (sweetener), or a sweetened food, drink or the like product comprising at least one derivative of the derivatives described above for the present invention as an effective component. In this case, it may optionally contain at least one substance selected from carriers and bulking agents for sweetening agents.

The above objects highlight certain aspects of the invention. Additional objects, aspects and embodiments of the invention are found in the following detailed description of the invention.

DETAILED DESCRIPTION OF THE INVENTION

Unless specifically defined, all technical and scientific terms used herein have the same meaning as commonly understood by a skilled artisan in chemistry, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The present invention is based, in part, on the inventor's discovery that N-alkylaspartyl amide derivatives represented by the following general formula (1), a salt form thereof, a sweetening agent (sweetener) and sweetened products such as a food and drink (food and/or drink) and the like comprising the derivative, possess superior stability, sweetening potency, and safety compared to sucrose, aspartame, and N-[N-(3,3-dimethylbutyl)-L-α-aspartyl]-L-phenylalanine 1-methyl esters described in the art.

In the present invention, the N-alkylaspartyl amide derivatives have the following formula:

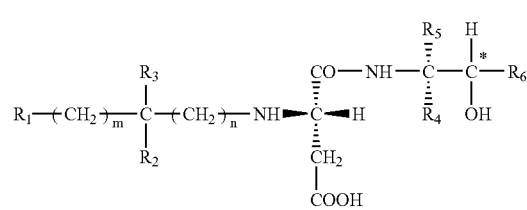

(1)

In formula (1), $R_1$ denotes any one of a hydroxyl group (OH), an alkoxy group having 1 to 4 carbon atoms (e.g., $OCH_3$, $OCH_2CH_3$), an alkoxycarbonyl group having 2 to 5 carbon atoms, and a phenyl or a substituted phenyl (phenyl having substituent group(s)) group represented by the following general formula (2), and

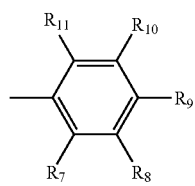

(2)

Where, in the above formula (2), $R_7$, $R_8$, $R_9$, $R_{10}$ and $R_{11}$ are reciprocally independent from each other and each denotes a substituent group selected from a hydrogen atom (—H), a hydroxyl group, an alkoxy group having 1 to 3 carbon atoms, and an alkyl group having 1 to 3 carbon atoms (e.g., $CH_3$, $CH_2CH_3$), wherein $R_7$ and $R_8$, or $R_8$ and $R_9$ may be combined together to form a methylene dioxy group ($OCH_2O$).

In formula (1), $R_2$ and $R_3$ are reciprocally independent from each other and each denotes a substituent group selected from a hydrogen atom and an alkyl group having 1 to 4 carbon atoms, or $R_2$ and $R_3$ are combined together to form an alkylene group having 2 to 5 carbon atoms (e.g., $CH_2CH_2$, $CH_2CH_2CH_2$). In formula (1), m and n are reciprocally independent from each other and each denotes a numerical value selected from 0, 1, 2, 3 and 4. C* indicates any steric configuration. Therefore, there is no particular limitations on the steric configuration at this position and any one configuration of (R), (S) and (RS) may be given thereto. In formula (1), q denotes 0 or 1.

$R_4$ and $R_5$, in formula (1) are reciprocally independent from each other and each denotes a substituent group selected from a hydrogen atom, an alkyl group having 1 to 6 carbon atoms, an alkoxyalkyl group having 2 to 7 carbon atoms, a hydroxyalkyl group having 1 to 6 carbon atoms, a phenyl group and a 2-furyl group, or $R_4$ and $R_5$ can be combined together to form an alkylene group having 2 to 5 carbon atoms. R6, in formula (1), denotes an alkyl group having 1 to 12 carbon atoms, a substituent group represented by the following general formula (3) or a substituent group represented by general formula (4), below:

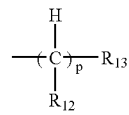

(3)

Where, in formula (3), $R_{12}$ denotes a substituent group selected from a hydrogen atom and an alkyl group having 1 to 4 carbon atoms, and $R_{13}$ denotes a carbocyclic compound residue group which contains three (3) to twelve (12)-membered ring(s), has substituent group(s) or no substituent group, and are saturated or unsaturated. In other words, $R_{13}$ is a carbocyclic compound (alicyclic compound) residue group containing three (3) to twelve (12)-membered ring(s), and with respect to the carbon-carbon bindings constituting the ring (s), may include any one of the residue group wherein all the carbon-carbon bindings constituting the compound are saturated (cycloalkyl group and the like), the residue group wherein at least one of the carbon-carbon bindings thereof is unsaturated (carbon-carbon double bond; cycloalkenyl group and the like, carbon-carbon triple bond; cycloalkynyl group and the like) and the like. In addition, on the carbon atom(s) constituting the ring(s) described above, the residue group may have at least one of the alkyl group(s) having 1 to 5 carbon atoms and/or other substituent group(s). In this case, further at least one carbon atom constituting said ring and the alkyl group(s) and/or other substituent group(s) described above may be combined to constitute an another ring and form a bicyclo alkyl group, a bicyclo alkenyl group, a tricyclo alkyl group or the like. Further, in formula (3) above, p denotes 0 or 1.

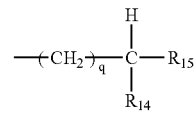

(4)

Where in formula (4), $R_{14}$ and $R_{15}$ are reciprocally independent from each other and each denotes a substituent group selected from a phenyl group, a hydrogen atom, a cycloalkyl group having 3 to 4 carbon atoms, an alkyl group having 1 to 6 carbon atoms, an alkoxyalkyl group having 2 to 7 carbon atoms and a 2-or 3-thienyl group, wherein said phenyl group may have at least one kind of the substituent groups selected from hydroxyl group(s), alkoxy group(s) having 1 to 3 carbon atoms, alkyl group (s) having 1 to 3 carbon atoms and methylene dioxy group(s).

In preferable derivatives in accordance with the present invention, which satisfy formula (1), $R_1$ is a phenyl group having at least one substituent group (one kind) of hydroxyl group(s), methyl group(s) and methoxy group(s), which may have plural substituent groups of the same kind (same in kind), or a hydroxyl group; $R_2$, $R_3$, $R_4$ and $R_5$ are reciprocally independent from each other and each is a hydrogen atom or a methyl group; $R_6$ is any one of a 2-phenylbutyl group, a 2-phenylbutyl group which has at least one substituent group selected from hydroxyl group(s), methoxy group(s) and methyl group(s) on the benzene ring, a cyclohexylmethyl group, and a cyclohexylmethyl group which has at least one substituent group selected from hydroxyl group(s), methoxy group(s) and methyl group(s) on the cyclohexane ring, a fenchylmethyl group, a norbornylmethyl group and a norbomylmethyl group which has at least one methyl group on the ring; and m and n are reciprocally independent from each other and each is 0 or an integer from 1 to 3.

More preferable derivatives of formula (1), include: $R_1$ is any one of a hydroxyl group, a 3-hydroxy-4-methoxyphenyl group, a 3-methoxy-4-hydroxyphenyl group, a 2-hydroxy-4-methoxyphenyl group, a 2,4-dihydroxyphenyl group, a 3-hydroxy-4-methylphenyl group, a 3-methyl-4-hydroxyphenyl group, a 4-hydroxyphenyl group, a 4-methoxyphenyl group and a 3-methyl-4-hydroxyphenyl group; $R_2$ is a hydrogen atom or a methyl group; $R_3$ is a hydrogen atom or a methyl group; $R_4$ is a hydrogen atom; $R_5$ is a methyl group; $R_6$ is a 2-phenylbutyl group or a cyclohexylmethyl group; m is 0 or any one of the integers from 1 to 3; and n is 0, 1 or 2.

In the formula described above, $R_6$ may be any one of (R)—, (S)— and (RS)-substituent groups, and particularly, any one of (R)—, (S)— and (RS)-2-phenylbutyl groups can be cited therefor as a preferable substituent group.

In the derivative of the present invention, when it is in a salt form, there is no limitation to a kind of the salt form. Particularly, when the derivative is used in a food and drink (food and/or drink), and also when said derivative having a salt form is used, a salt acceptable for use in a food and drink can be employed.

Further, in another embodiment, the present invention provides a sweetening agent (sweetener), or a sweetened food, drink or the like product comprising at least one derivative in accordance with the present invention as an effective component. In this case, the sweetening agent may optionally contain at least one substance selected from carriers and bulking agents for sweetening agents.

For the derivative(s) used as an effective component in this invention, one kind of the derivative (one compound in increments of compound included in the foregoing formula (1)), or multiple kinds of the derivatives may be employed in the sweetening agents, foods, and/or drinks.

If one kind of the derivative (one compound) is employed, a free form thereof, salt form(s) thereof (one or more kinds) or a mixture thereof can be employed. And, when multiple kinds of the derivatives are employed, in each compound, a free form thereof, salt form(s) thereof (one or more kinds) or a mixture thereof can be employed.

In the novel N-alkylaspartyl amide derivative of the present invention, the compounds represented by the foregoing general formula (1), and their salt forms are included.

The aspartic acid constituting the above-described derivative is preferably in the L-form ((S)-form), and however a stereochemistry (stereochemical structure) for each asymmetric center in the amine components (moieties) may be in any form of (R), (S) and (RS) forms.

In the compounds to be included in the above-described derivative(s) of the present invention, the following contents are contained as preferable examples.

[1]
A compound represented by the above-mentioned formula (1); provided that in formula (1), $R_1$ denotes any one of a hydroxyl group (OH), an alkoxy group having 1 to 4 carbon atoms ($OCH_3$, $OCH_2CH_3$ and the like), an alkoxycarbonyl group having 1 to 4 carbon atoms, or a substituent group represented by the foregoing general formula (2) (a substituted or a non-substituted phenyl group; phenyl group having substituent group(s) or no substituent group).

In the foregoing general formula (2), $R_7$, $R_8$, $R_9$, $R_{10}$ and $R_{11}$ are reciprocally independent from each other and each denotes a substituent group selected from a hydrogen atom (H), a hydroxyl group, an alkoxy group having 1 to 3 carbon atoms and an alkyl group having 1 to 3 carbon atoms (e.g., $CH_3$, $CH_2CH_3$), wherein $R_7$ and $R_8$, or $R_8$ and $R_9$ may be combined together to form a methylene dioxy group ($OCH_2O$).

In such case, when $R_7$, $R_8$, $R_9$, $R_{10}$ and $R_{11}$ are all hydrogen atoms, the substituent group of the formula (2) denotes a phenyl group with no substituent group, which is a phenyl group. On the other hand, the substituted phenyl group is a group having at least one kind of the above-described substituent groups other than the hydrogen atom at the benzene ring.

Examples of suitable substituted phenyl groups include: a 3-hydroxy-4-methoxyphenyl group, a 3-methoxy-4-hydroxyphenyl group, a 2,4-dihydroxyphenyl group, a 4-methoxyphenyl group, a 3-hydroxyphenyl group, a 3-methyl-4-hydroxyphenyl group, a 3,4-methylene dioxy phenyl group, a 3-hydroxy-4-methylphenyl group, a 2-hydroxy-4-methylphenyl group and the like.

In the above formula (1), $R_2$ and $R_3$ are reciprocally independent from each other and each denotes a substituent group selected from a hydrogen atom and an alkyl group having 1 to 4 carbon atoms, or $R_2$ and $R_3$ are combined together to denote an alkylene group having 2 to 5 carbon atoms (e.g., $CH_2CH_2$, $CH_2CH_2CH_2$).

m and n are reciprocally independent from each other and each denotes a numerical value selected from 0, 1, 2, 3 and 4, and preferably 0 or an integer from 1 to 3.

$R_4$ and $R_5$ are reciprocally independent from each other and each denotes a substituent group selected from a hydrogen atom, an alkyl group having 1 to 6 carbon atoms, an alkoxyalkyl group having 2 to 7 carbon atoms, a hydroxyalkyl group having 1 to 6 carbon atoms, a phenyl group and a 2-furyl group, or $R_4$ and $R_5$ are combined together to denote an alkylene group having 2 to 5 carbon atoms.

$R_6$ denotes an alkyl group having 1 to 12 carbon atoms, a substituent group represented by the foregoing general formula (3) or a substituent group represented by the foregoing general formula (4).

In the above formula (3), $R_{12}$ denotes a substituent group selected from a hydrogen atom and an alkyl group having 1 to 4 carbon atoms.

$R_{13}$ denotes a carbocyclic compound (or alicyclic compound) residue group which contains three (3) to twelve (12)-membered ring(s), has substituent group(s) or no substituent group, and are saturated or unsaturated. Namely, it is a carbocyclic compound (or alicyclic compound) residue group which contains three (3) to twelve (12)-membered ring(s), and as for the carbon-carbon binding(s) constituting the ring, there are no particular limitations. For examples, the residue group wherein all the carbon-carbon bindings constituting the compound are saturated (cycloalkyl group and the like), the residue group wherein at least one of the carbon-carbon bindings thereof is unsaturated (carbon-carbon double bond; cycloalkenyl group and the like, carbon-carbon triple bond; cycloalkynyl group and the like) and the like may be included therein. In addition, on the carbon atom(s) constituting the ring described above, the residue group may have at least one kind of the alkyl group(s) having 1 to 5 carbon atoms and/or other substituent group(s). In this case, further at least one carbon atom constituting said ring and the alkyl group(s) and/or other substituent group(s) described above may be combined to constitute an another ring and form a bicyclo alkyl group, a bicyclo alkenyl group, a tricyclo alkyl group or the like.

For examples of such carbocyclic compound residue group, for examples, a cyclopropyl group, a cyclopentyl group, a cyclodecanyl group, a cyclohexyl group, a 2,5-cyclohexadienyl group, a 2,6-dimethylcyclohexyl group, a fenchyl group, a norbornyl group, a 3-methyl-norbornyl group, a 1-methyl-norbornyl group, a 3,3-dimethyl-norbornyl group and the like can be cited.

In the above formula (3), p denotes 0 or 1.

In the above formula (4), $R_{14}$ and $R_{15}$ are reciprocally independent from each other and each denotes a substituent group selected from a phenyl group, a hydrogen atom, a cycloalkyl group having 3 to 4 carbon atoms, an alkyl group having 1 to 6 carbon atoms, an alkoxyalkyl group having 2 to 7 carbon atoms and a 2-or 3-thienyl group.

Said phenyl group may have at least one kind of the substituent groups selected from hydroxyl group(s), alkoxy group(s) having 1 to 3 carbon atoms, alkyl group (s) having 1 to 3 carbon atoms and methylene dioxy group(s). In this case, it may have plural (more than one) substituent groups of the same kind (same in kind).

For examples of such phenyl group, for example, a phenyl group with no substituent group, a 3-hydroxy-4-methoxyphenyl group, a 3-methoxy-4-hydroxyphenyl group, a 2,4-dihydroxyphenyl group, a 4-methoxyphenyl group, a 3-methyl-4-hydroxyphenyl group, a 3,4-methylene dioxy phenyl group, a 4-hydroxyphenyl group, a 4-methylphenyl group and the like can be cited.

q denotes 0 or 1.

For preferable derivatives, the derivatives described above in the above present invention, wherein in said formula (1) described above, $R_1$ is a phenyl group having at least one substituent group (one kind) of hydroxyl group(s), methyl group(s) and methoxy group(s), which may have plural substituent groups of the same kind (same in kind), or a hydroxyl group, $R_2$, $R_3$, $R_4$ and $R_5$ are reciprocally independent from each other and each is a hydrogen atom or a methyl group, $R_6$ is any one of a 2-phenylbutyl group, a 2-phenylbutyl group which has at least one substituent group selected from hydroxyl group(s), methoxy group(s) and methyl group(s) on the benzene ring, a cyclohexylmethyl group, and a cyclohexylmethyl group which has at least one substituent group selected from hydroxyl group(s), methoxy group(s) and methyl group(s) on the cyclohexane ring, a fenchylmethyl group, a norbomylmethyl group and a norbomylmethyl group which has at least one methyl group on the ring, and m and n are reciprocally independent from each other and each is 0 or an integer from 1 to 3, can be cited.

For more preferable derivatives, the derivatives described above in the above present invention, wherein in said formula (1) described above, $R_1$ is any one of a hydroxyl group, a 3-hydroxy-4-methoxyphenyl group, a 3-methoxy-4-hydroxyphenyl group, a 2-hydroxy-4-methoxyphenyl group, a 2,4-dihydroxyphenyl group, a 3-hydroxy-4-methylphenyl group, a 3-methyl-4-hydroxyphenyl group, a 4-hydroxyphenyl group, a 4-methoxyphenyl group and a 3-methyl-4-hydroxyphenyl group, $R_2$ is a hydrogen atom or a methyl group, $R_3$ is a hydrogen atom or a methyl group, $R_4$ is a hydrogen atom, $R_5$ is a methyl group, $R_6$ is a 2-phenylbutyl group or a cyclohexylmethyl group, m is 0 or any one of the integers from 1 to 3, and n is 0, 1 or 2, can be cited.

[2]

The compound as described above in [1], wherein $R_1$ is a 3-hydroxy-4-methoxyphenyl group, $R_2$, $R_3$ and $R_4$ are a hydrogen atom, $R_5$ is a methyl group, $R_6$ is a (R), (S) or (RS)-2-phenylbutyl group, and m and n are 1, and the steric configuration for the C* is in any one of the (R), (S) and (RS) forms.

[3]

The compound as described above in [1], wherein $R_1$ is a 3-methoxy-4-hydroxyphenyl group, $R_2$, $R_3$ and $R_4$ are a hydrogen atom, $R_5$ is a methyl group, $R_6$ is a (R), (S) or (RS)-2-phenylbutyl group, and m and n are 1, and the steric configuration for the C* is in any one of the (R), (S) and (RS) forms.

[4]

The compound as described above in [1], wherein $R_1$ is a 2-hydroxy-4-methoxyphenyl group, $R_2$, $R_3$ and $R_4$ are a hydrogen atom, $R_5$ is a methyl group, $R_6$ is a (R), (S) or (RS)-2-phenylbutyl group, and m and n are 1, and the steric configuration for the C* is in any one of the (R), (S) and (RS) forms.

[5]

The compound as described above in [1], wherein $R_1$ is a 2,4-dihydroxyphenyl group, $R_2$, $R_3$ and $R_4$ are a hydrogen atom, $R_5$ is a methyl group, $R_6$ is a (R), (S) or (RS)-2-phenylbutyl group, and m and n are 1, and the steric configuration for the C* is in any one of the (R), (S) and (RS) forms.

[6]

The compound as described above in [1], wherein $R_1$ is a 3-hydroxy-4-methylphenyl group, $R_2$, $R_3$ and $R_4$ are a hydrogen atom, $R_5$ is a methyl group, $R_6$ is a (R), (S) or (RS)-2-phenylbutyl group, and m and n are 1, and the steric configuration for the C* is in any one of the (R), (S) and (RS) forms.

[7]

The compound as described above in [1], wherein $R_1$ is a 3-methyl-4-hydroxyphenyl group, $R_2$, $R_3$ and $R_4$ are a hydrogen atom, $R_5$ is a methyl group, $R_6$ is a (R), (S) or (RS)-2-phenylbutyl group, and m and n are 1, and the steric configuration for the C* is in any one of the (R), (S) and (RS) forms.

[8]

The compound as described above in [1], wherein $R_1$ is a 4-hydroxyphenyl group, $R_2$, $R_3$ and $R_4$ are a hydrogen atom, $R_5$ is a methyl group, $R_6$ is a (R), (S) or (RS)-2-phenylbutyl group, and m and n are 1, and the steric configuration for the C* is in any one of the (R), (S) and (RS) forms.

[9]

The compound as described above in [1], wherein $R_1$ is a 4-methoxyphenyl group, $R_2$, $R_3$ and $R_4$ are a hydrogen atom, $R_5$ is a methyl group, $R_6$ is a (R), (S) or (RS)-2-phenylbutyl group, and m and n are 1, and the steric configuration for the C* is in any one of the (R), (S) and (RS) forms.

[10]

The compound as described above in [1], wherein $R_1$ is a 3-hydroxy-4-methoxyphenyl group, $R_2$, $R_3$ and $R_5$ are a methyl group, $R_4$ is a hydrogen atom, $R_6$ is a (R), (S) or (RS)-2-phenylbutyl group, m is 0, and n is 2, and the steric configuration for the C* is in any one of the (R), (S) and (RS) forms.

[11]

The compound as described above in [1], wherein $R_1$ is a 3-methyl-4-hydroxyphenyl group, $R_2$, $R_3$ and $R_5$ are a methyl group, $R_4$ is a hydrogen atom, $R_6$ is a (R), (S) or (RS)-2-phenylbutyl group, m is 0, and n is 2, and the steric configuration for the C* is in any one of the (R), (S) and (RS) forms.

[12]

The compound as described above in [1], wherein $R_1$ is a 3-hydroxy-4-methoxyphenyl group, $R_2$, $R_3$ and $R_4$ are a hydrogen atom, $R_5$ is a methyl group, $R_6$ is a cyclohexylmethyl group, and m and n are 1, and the steric configuration for the C* is in any one of the (R), (S) and (RS) forms.

[13]

The compound as described above in [1], wherein $R_1$ is a 3-hydroxy-4-methoxyphenyl group, $R_2$, $R_3$ and $R_5$ are a methyl group, $R_4$ is a hydrogen atom, $R_6$ is a cyclohexylmethyl group, m is 0, and n is 2, and the steric configuration for the C* is in any one of the (R), (S) and (RS) forms.

[14]

The compound as described above in [1], wherein $R_1$ is a hydroxyl group, $R_2$, $R_3$ and $R_5$ are a methyl group, $R_4$ is a hydrogen atom, $R_6$ is a (R), (S) or (RS)-2-phenylbutyl group, and m and n are 2, and the steric configuration for the C* is in any one of the (R), (S) and (RS) forms.

[15]

The compound as described above in [1], wherein $R_1$ is a hydroxyl group, $R_2$, $R_3$ and $R_5$ are a methyl group, $R_4$ is a hydrogen atom, $R_6$ is a (R), (S) or (RS)-2-phenylbutyl group, m is 3, and n is 2, and the steric configuration for the C* is in any one of the (R), (S) and (RS) forms.

[16]

The compound as described above in any one of the above items [1] to [15], wherein the amino acid (aspartic acid) constituting the derivative is in the L-form or D-form (enantiomer; optical isomer of the derivative represented by the foregoing formula (1)).

In the derivative(s) of the present invention, various salt forms derived from the compound(s) described above or the compound(s) in the salt form(s) are included.

As an another embodiment, further the following contents are contained in the present invention.

[17]

A sweetening agent (sweetener), or a sweetened food, drink or the like product comprising at least one derivative (one kind) described above (which include the foregoing compounds and the salt forms thereof) as an effective component. In this case, it may contain at least one substance selected from carriers and bulking agents for sweetening agents.

[18]

A method for imparting sweetness, comprising a step of: including (mixing or adding) at least one derivative (one kind) of the derivatives (which include the foregoing compounds and the salt forms thereof) in the present invention in (to) a product in need of sweetness, such as food and/or drink (beverage), pharmaceutical product, oral hygiene product or the like.

The derivatives of the present invention include the compounds represented by the foregoing formula (1) and their salt forms. Examples of suitable salts may be enumerated by, for example, salts of the compounds with alkali metals (such as sodium and potassium), salts of the compounds with alkali earth metals (such as calcium and magnesium), ammonium salts of the compounds with ammonia and the like, salts of the compounds with amino acids (such as lysine and arginine), salts of the compounds with inorganic acids (such as hydrogen chloride and sulfuric acid), salts of the compounds with organic acids (such as citric acid and acetic acid), and salts of the compounds with another sweetening agent(s) or the ingredients thereof, including saccharin, acesulfame, cyclamic acid, glycyrrhizic acid and the like. These salts may be included in the derivatives of the present invention, as pointed out above.

In order to produce these salts, a salt-formation process, which has been known or used conventionally in the art, may be applied. For example, in an appropriate medium, such as a water or an another solvent, the compound (free form) contained in the derivatives of the present invention, is reacted with the acid, the alkali, or the sweetening agent or the like described above to produce easily a desired salt.

The aspartyl amide derivative to use for synthesis of the derivative of the present invention may be obtained by a usual peptide synthesis method, as discussed in Izumiya et al, Fundamentals and Experimentation in Peptide Synthesis, published by MARUZEN on Jan. 20, 1985. In this process, first an amino alcohol is reacted with L-aspartic acid wherein the β-carboxyl group and the amino group are protected, for condensation to obtain an amide, and then the protective groups (protecting groups) are removed therefrom, or first L-aspartic acid wherein the β-carboxyl group and the amino group are protected, is converted into its activated ester, thus obtained ester is reacted with an amino alcohol to obtain an amide, and then the protective groups are removed therefrom, whereby the desired α-L-aspartyl amide can be obtained. The method for synthesis of the derivatives in the present invention, particularly the foregoing compounds is, however, not limited thereto.

An N-alkyl aspartyl amide derivative can be easily synthesized through reductive alkylation of the foregoing aspartyl amide derivative with an aldehyde or ketone and a reducing agent (for example, hydrogen/palladium-carbon catalyst or the like). Or, an amide of the L-aspartic acid having protective groups with an amino alcohol is obtained, and then the N-protective group is selectively removed therefrom, and it is alkylated reductively using an aldehyde or ketone (refer to A. F. Abdel—Magid et al, Tetrahedron letters, 31, 5595 (1990)), followed by removal of the remaining protective group, to be able to obtain the same. In this process, first an amino alcohol is reacted with the L-aspartic acid wherein the β-carboxyl group and the amino group are protected, for condensation to obtain an amide, or firstly the L-aspartic acid wherein the β-carboxyl group and the amino group are protected, is converted into its activated ester, and thus obtained ester is reacted with an amino alcohol to obtain an amide. The N-protective group in the protected aspartyl amide thus obtained is selectively removed therefrom, and the thus obtained product is alkylated reductively with an aldehyde or ketone and a reducing agent (for example, $NaB(OAc)_3H$), followed by removal of the remaining protective group, to be able to obtain the desired N-alkyl-α-L-aspartyl amide. The method for synthesis of the foregoing compounds in the present invention is, however, not limited thereto. An amino alcohol used for the compound in the present invention can be obtained easily from an amino acid as an optically active substance according to the method described in the literature (refer to M. W. Holladay et al, Tetrahedron Letters, 24, 4401 (1983), M. T. Reetz et al, Angew. Chem. Int. Ed. Engle., 26, 1141 (1987) and the like) or the like. The method for synthesis thereof is, however, not limited thereto. In place of the foregoing aldehyde or ketone, the acetal or ketal derivative therefrom can, of course, be used as a component of the aldehyde or ketone for the reductive alkylation.

As a result of sensory (organoleptic) tests, the derivatives of the present invention (i.e., the compounds and the salt forms thereof of the present invention), have been found to have a strong sweetening potency and a quality of sweetness similar to that of sugar. For example, the sweetening potency of N-[3-(3-hydroxy-4-methoxyphenyl)propyl]-α-L-aspartyl N-(1R,2S,4S)-1-methyl-2-hydroxy-4-phenylhexyl amide was approximately 15000 times that of sugar, and the sweetening potency of N-[3-methyl-3-(3-hydroxy-4-methoxyphenyl)butyl]-α-L-aspartyl N-(1R,2S,4S)-1-methyl-2-hydroxy-4-phenylhexyl amide was approximately 15000 times that of sugar.

On the other hand, the inventors of the present invention have found that the half life of N-[3-methyl-3-(3-hydroxy-4-methoxyphenyl)butyl]-α-L-aspartyl N-(1R,2S,4S)-1-methyl-2-hydroxy-4-phenylhexyl amide and the half life of N-(3,3-dimethyl-5-hydroxypentyl)-α-L-aspartyl N-(1R,2S,4S)-1-methyl-2-hydroxy-4-phenylhexyl amide in an acidic aqueous solution (phosphate buffer of pH=3 at 70° C.) were approximately 132 hours and approximately 125 hours, respectively, and therefore they are far more stable in comparison to the aspartame (half life: approximately 30 hours).

Table 1 below, reproduced from Example 19, shows the structures and the results of the sensory tests on the several synthesized N-alkyl aspartyl amide derivatives, represented by the following general formula (5).

As may be seen from the results of the Table 1, the novel derivatives of the present invention are particularly excellent in degree of sweetness (sweetening potency).

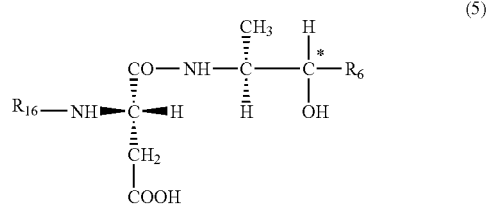

(5)

In the above formula (5), $R_6$ and $C^*$ have the same meanings or definitions as the $R_6$ and $C^*$ used in the foregoing formula (1), and the explanations for the $R_6$ and $C^*$ described there are also applied thereto. $R_{16}$ means any one of the substituent groups shown in the following Table 1.

Meanwhile, in case that the derivatives of the present invention (compounds of the present invention inclusive of salt forms thereof) are used as a sweetening agent, it is of course possible to use other sweetening agent(s) in combination.

If the derivatives of the present invention are used as a sweetening agent, it may be of course possible to use carrier(s) and/or bulking agent(s), for example, the carrier(s) and/or the bulking agent(s) known or used so far, in combination therewith.

For the carrier(s) and/or the bulking agent(s), one or more compounds of, for example, polydextrose, starch, maltodextrines, cellulose, methylcellulose, carboxymethylcellulose, and other cellulose derivatives, sodium alginate, pectins, gums, lactose, maltose, glucose, sucrose, leucine, glycerole, mannitol, sorbitol, xylitol, erythritol, and the equivalents thereof.

The derivatives of the present invention can be used as a sweetening agent or an ingredient (component) thereof. In addition, the derivatives of the present invention can be used as a sweetening agent for products, such as foods and/or drinks or the like products, in need of a sweet taste, such as confectionery, chewing gums, hygiene products, toiletries, cosmetics, pharmaceutical products and various veterinary products for animals other than those for humans. Moreover,

TABLE 1

Structure of N-alkyl aspartyl amide derivative and Sweetening potency:

| Compound Sweetening No. | $R_{16}$[1] | C*Configuration (S:R) | $R_6$[2] | Potency[3] |
|---|---|---|---|---|
| 1 | 3-(3-OH-4-OMe—Ph)propyl | >5:1 | (S)-2-phenylbutyl | 15000 |
| 2 | 3-(3-OMe-4-OH—Ph)propyl | >5:1 | (S)-2-phenylbutyl | 10000 |
| 3 | 3-(2-OH-4-OMe—Ph)propyl | >5:1 | (S)-2-phenylbutyl | 6000 |
| 4 | 3-(2,4-di.OH—Ph)propyl | >5:1 | (S)-2-phenylbutyl | 10000 |
| 5 | 3-(3-OH-4-Me—Ph)propyl | >5:1 | (S)-2-phenylbutyl | 6000 |
| 6 | 3-(3-Me-4-OH—Ph}propyl | >5:1 | (S)-2-phenylbutyl | 4000 |
| 7 | 3-(4-OH—Ph)propyl | >5:1 | (S)-2-phenylbutyl | 6000 |
| 8 | 3-(4-OMe—Ph)propyl | >5:1 | (S)-2-phenylbutyl | 3000 |
| 9 | 3-Me-3-(3-OH-4-OMe—Ph)butyl | >5:1 | (S)-2-phenylbutyl | 15000 |
| 10 | 3-Me-3-(3-Me-4-OH—Ph)butyl | >5:1 | (S)-2-phenylbutyl | 15000 |
| 11 | 3-(3-OH-4-OMe—Ph)propyl | >9:1 | (R)-2-phenylbutyl | 4000 |
| 12 | 3-(3-OH-4-OMe—Ph)propyl | 3:7 | cyclohexylmethyl | 4000 |
| 13 | 3-(3-OH-4-OMe—Ph)propyl | 1:>9 | cyclohexylmethyl | 5000 |
| 14 | 3-Me-3-(3-OH-4-OMe—Ph)butyl | 1:>9 | cyclohexylmethyl | 5000 |
| 15 | 3,3-di.Me-5-OH-pentyl | >5:1 | (S)-2-phenylbutyl | 6500 |
| 16 | 3,3-di.Me-6-OH-hexyl | >5:1 | (S)-2-phenylbutyl | 4500 |

[1] OH: hydroxy, OMe: methoxy, Me: methyl, Ph: phenyl, di-OH: dihydroxy, di-Me: dimethyl;
[2] steric configuration (R or S) defined based on the structure in the form wherein $R_6$ is bonded to C* carbon; and
[3] values compared to sweetening potency of a 4% aqueous solution of sucrose.

In the description of the present application or the above Table, ">5" represents a numerical value of more than 5, and ">9" denotes a numerical value of more than 9, respectively. And, in the above Table, regarding the steric configuration of the 2-phenylbutyl group, the configuration is shown when the group is observed in the molecule on the whole. Therefore, the (S) configuration as shown there means a (S) configuration when the 2-phenylbutyl group is observed in the molecule on the whole, and on the other hand, it means a (R) configuration when the substituent group as such only is watched and observed.

the derivatives of the present invention can be used in the form of a sweetened product containing the derivative(s) of the present invention, and also in the method for imparting a sweet taste (sweetness) to the products (foods or the like products) in need of a sweet taste. As for the method of using the derivatives of the present invention, any suitable conventional or well-known method for using a sweetening agent can be applied thereto.

Having generally described this invention, a further understanding can be obtained by reference to certain specific examples, which are provided herein for purposes of illustration only, and are not intended to be limiting unless otherwise specified.

EXAMPLES

In the following Examples, the NMR spectra and the MS spectra were measured using a Bruker AVANCE400 (400 MHz) and a Thermo Quest TSQ700, respectively.

Example 1

Synthesis of N-t-butoxycarbonyl-β-O-benzyl-α-L-aspartyl N-(1R,2S,4S)-1-methyl-2-hydroxy-4-phenylhexyl amide Lithium aluminium hydride (lithium aluminohydride; LAH) (0.73 g, 19.25 mmol) was suspended in ether (50 ml) and the resulting suspension was maintained at 0° C. N-Methoxy-N-methylcarboxy amide of N,N-dibenzyl-α-D-alanine (3.44 g, 11.0 mmol) was added thereto. The mixture was stirred at 0° C. for 1 hour, and then 50 ml of a 1M potassium hydrogen sulfate aqueous solution was added thereto. From the reaction solution, two ether extractions were performed and the resulting organic layer was washed with a 5% sodium hydrogen carbonate aqueous solution (50 ml) and a saturated saline aqueous solution (50 ml), and then dried with anhydrous magnesium sulfate. The magnesium sulfate was filtered off and the liquid filtrate was concentrated under reduced pressure to yield (R)-2-N,N-dibenzylaminopropyl aldehyde (2.76 g, 10.9 mmol).

Magnesium (0.24 g, 9.9 mmol) was suspended in tetrahydrofuran (THF; 1 ml), and a solution of (R)-2-phenyl butyl bromide (1.41 g, 6.6 mmol) dissolved in THF (2 ml) was added dropwise. The reaction solution was stirred at room temperature for 1 hour and THF (5 ml) was subsequently added and the solution was cooled to 0° C. To the reaction solution, a solution of (R)-2-N,N-dibenzylaminopropyl aldehyde (1.37 g, 5.5 mmol) dissolved in THF (10 ml) was added and the resulting solution was stirred at 0° C. for 1 hour. To the reaction solution, a saturated ammonium chloride aqueous solution (50 ml) was added, and two 50 ml ether extractions were performed. The resulting organic layer was washed with a 5% sodium hydrogen carbonate aqueous solution (50 ml) and a saturated saline aqueous solution (50 ml), and then dried with anhydrous magnesium sulfate. Magnesium sulfate was filtered off for removal and the liquid filtrate was concentrated under reduced pressure. The resulting residue was purified by preparative thin layer chromatography (PTLC) to yield N,N-dibenzyl-(1R,2S,4S)-1-methyl-2-hydroxy-4-phenylhexyl amine (2S:2R=>5:1) (1.46 g, 3.77 mmol).

The N,N-dibenzyl-(1R,2S,4S)-1-methyl-2-hydroxy-4-phenylhexyl amine (1.46 g, 3.77 mmol) obtained above was dissolved in methanol (25 ml). Subsequently, acetic acid (0.43 ml, 7.53 mmol) and 5% Pd-C (palladium carbon; containing 50% of water) (0.6 g) were added to the dissolved solution. This reaction solution was stirred for 16 hours at 50° C. under a hydrogen atmosphere, and the catalyst was filtered off. The liquid filtrate thus obtained was concentrated under reduced pressure. To the resulting residue, a saturated sodium hydrogen carbonate aqueous solution (15 ml) was added and two 50 ml methylene chloride extractions were performed. The resulting organic layer was dried with anhydrous magnesium sulfate. Magnesium sulfate was filtered off and the liquid filtrate was concentrated under reduced pressure to yield (1R,2S,4S)-1-methyl-2-hydroxy-4-phenylhexyl amine (0.61 g, 2.96 mmol).

To methylene chloride (30 ml), N-t-butoxycarbonyl-L-aspartic acid-β-benzyl ester (0.91 g, 2.80 mmol) and the above described (1R,2S,4S)-1-methyl-2-hydroxy-4-phenylhexyl amine (0.58 g, 2.80 mmol) were added. The reaction solution was cooled to 0° C., and water-soluble carbodiimide hydrochloride (0.59 g, 3.08 mmol) and 1-hydroxybenzotriazole monohydrate (HOBt) (0.42 g, 3.08 mmol) were added. The resulting solution was stirred for 1 hour with cooling and stirred overnight at room temperature. The reaction mixture was concentrated under reduced pressure, and to the resulting residue, water (50 ml) was added and two ethyl acetate extractions (50 ml) were performed. The resulting organic layer was washed twice with a 5% citric acid aqueous solution (50 ml), with water (50 ml), twice with a 5% sodium hydrogen carbonate aqueous solution (50 ml) and with a saturated saline aqueous solution (50 ml). The organic layer was dried with anhydrous magnesium sulfate and magnesium sulfate was filtered off. The liquid filtrate was concentrated at reduced pressure to yield N-t-butoxycarbonyl-β-O-benzyl-α-L-aspartyl N-(1R,2S,4S)-1-methyl-2-hydroxy-4-phenylhexyl amide (1.43 g, 2.78 mmol) as a viscous oily matter.

Example 2

Synthesis of N-t-butoxycarbonyl-β-O-benzyl-α-L-aspartyl N-(1R,2RS)-1-methyl-2-hydroxy-3-cyclohexylpropyl amide LAH (0.66 g, 17.5 mmol) was suspended in ether (40 ml) and the resulting suspension was kept at 0° C. N-Methoxy-N-methylcarboxy amide of N-t-butoxycarbonyl-α-D-alanine (2.32 g, 10.0 mmol) was added thereto. The mixture was stirred at 0° C. for 1 hour, and then 1M potassium hydrogen sulfate aqueous solution (25 ml) was added thereto. From the reaction solution, two ether extractions (50 ml) were performed, and the resulting organic layer was washed with a 5% sodium hydrogen carbonate aqueous solution (50 ml) and a saturated saline aqueous solution (50 ml), and subsequently dried with anhydrous magnesium sulfate. Magnesium sulfate was filtered off and the liquid filtrate was concentrated at a reduced pressure to yield (R)-2-N-t-butoxycarbonylaminopropyl aldehyde (1.29 g, 7.43 mmol) as a solid matter.

Magnesium (0.68 g, 27.8 mmol) was suspended in THF (2 ml), and a solution of cyclohexylmethyl bromide (3.29 g, 18.6 mmol) dissolved in THF (3 ml) was added dropwise thereto. The reaction solution was stirred at room temperature for 1 hour and THF (5 ml) was added, and the solution was cooled to −78° C. To the reaction solution, a solution of (R)-2-N-t-butoxycarbonylaminopropyl aldehyde (1.29 g, 7.43 mmol) produced previously dissolved in THF (10 ml) was added and the resulting solution was slowly heated from −78° C., and stirred at room temperature for 15 hours. To the reaction solution, a saturated ammonium chloride aqueous solution (50 ml) was added, and two ether extractions (50 ml) were performed. The resulting organic layer was washed with a 5% sodium hydrogen carbonate aqueous solution (50 ml) and a saturated saline aqueous solution (50 ml), and then dried with anhydrous magnesium sulfate. Magnesium sulfate was filtered off and the liquid filtrate was concentrated at a reduced pressure. The resulting residue was purified by PTLC to yield (1R,2RS)-N-t-butoxycarbonyl-1-methyl-2-hydroxy-3-cyclohexylpropyl amine (2S:2R=3:7) (0.88 g, 3.25 mmol) as an oily matter.

To the (1R,2RS)-N-t-butoxycarbonyl-1-methyl-2-hydroxy-3-cyclohexylpropyl amine (0.88 g, 3.25 mmol), 4N-HCl/dioxane solution (15 ml) was added. The resulting mixture was stirred at room temperature for 1 hour. The reaction solution was concentrated under reduced pressure, ether (25 ml) was added to the thus obtained residue, and the solution was then further concentrated. The resulting residue was dissolved in methylene chloride (30 ml) and this reaction solution was cooled to 0° C., and N-t-butoxycarbonyl-L-aspartic acid-β-benzyl ester (1.11 g, 3.42 mmol), triethylamine (0.50 ml, 3.58 mmol), water soluble carbodiimide (0.69 g, 3.58 mmol) and HOBt (0.48 g, 3.58 mmol) were added thereto. The reaction solution was stirred for 1 hour with cooling and stirred overnight at room temperature.

The reaction solution was subsequently concentrated at a reduced pressure, and to the resulting residue, water (50 ml) was added and two ethyl acetate extractions (50 ml) were performed. The resulting organic layer was washed twice with a 5% citric acid aqueous solution (50 ml), with water (50 ml), twice with a 5% sodium hydrogen carbonate aqueous solution (50 ml) and with a saturated saline aqueous solution (50 ml). The organic layer was dried with anhydrous magnesium sulfate. Subsequently the magnesium sulfate was filtered off and the liquid filtrate was concentrated at a reduced pressure followed by purification by PTLC to yield N-t-butoxycarbonyl-β-O-benzyl-α-L-aspartyl N-(1R,2RS)-1-methyl-2-hydroxy-3-cyclohexylpropyl amide (0.81 g, 1.69 mmol) as a viscous oily matter.

Example 3

Synthesis of N-[3-(3-hydroxy-4-methoxyphenyl) propyl]-α-L-aspartyl N-(1R,2S,4S)-1-methyl-2-hydroxy-4-phenylhexyl amide (Table 1; Compound No.1)

To N-t-butoxycarbonyl-β-O-benzyl-α-L-aspartyl N-(1R,2S,4S)-1-methyl-2-hydroxy-4-phenylhexyl amide (831 mg, 1.62 mmol) obtained in the Example 1, 4N-HCl/dioxane solution (10 ml) was added, and the mixture was stirred at room temperature for 1 hour. The reaction solution was concentrated under reduced pressure, and 5% sodium hydrogen carbonate aqueous solution (50 ml) was added thereto. Two ethyl acetate extractions (50 ml) were subsequently performed. The organic layer was washed with a saturated saline aqueous solution (50 ml) and then dried with anhydrous magnesium sulfate. Magnesium sulfate was filtered off and the liquid filtrate was concentrated at a reduced pressure to yield β-O-benzyl-α-L-aspartyl N-(1R,2S,4S)-1-methyl-2-hydroxy-4-phenylhexyl amide (641 mg, 1.55 mmol).

The above described β-O-benzyl-α-L-aspartyl N-(1R,2S,4S)-1-methyl-2-hydroxy-4-phenylhexyl amide (641 mg, 1.55 mmol) was dissolved in THF (20 ml) and the solution was maintained at 0° C. 3-(3-Benzyloxy-4-methoxyphenyl) cinnamaldehyde (416 mg, 1.55 mmol), acetic acid (0.09 ml, 1.55 mmol) and NaB(OAc)$_3$H (493 mg, 2.33 mmol) were added thereto. The resulting mixture was stirred for 1 hour at 0° C. and further stirred overnight at room temperature. To the reaction solution, a saturated sodium hydrogen carbonate aqueous solution (15 ml) was added, and two ethyl acetate extractions (50 ml) were performed. The organic layer was washed with a saturated saline aqueous solution (50 ml) and then dried with anhydrous magnesium sulfate. Magnesium sulfate was filtered off and the liquid filtrate was concentrated at a reduced pressure. The resulting residue was purified by PTLC to yield N-[3-(3-benzyloxy-4-methoxyphenyl)propyl]-β-O-benzyl-α-L-aspartyl N-(1R,2S,4S)-1-methyl-2-hydroxy-4-phenylhexyl amide (805 mg, 1.21 mmol) as a viscous oily matter.

The above described N-[3-(3-benzyloxy-4-methoxyphenyl)propyl]-β-O-benzyl-α-L-aspartyl N-(1R,2S,4S)-1-methyl-2-hydroxy-4-phenylhexyl amide (805 mg, 1.21 mmol) was dissolved in methanol (20 ml), and 10% palladium carbon (containing 50% of water) (400 mg) was added thereto. The resulting mixture was reacted for 5 hours at room temperature under a hydrogen atmosphere. The catalyst was filtered off and the liquid filtrate was concentrated at a reduced pressure. The resulting residue was purified by PTLC to yield N-[3-(3-hydroxy-4-methoxyphenyl) propyl]-α-L-aspartyl N-(1R,2S,4S)-1-methyl-2-hydroxy-4-phenylhexyl amide (251 mg, 0.52 mmol) as a solid matter. The compound could be crystallized with the use of a mixed solvent of water-methanol.

$^1$HNMR (DMSO-d$_6$) δ: 0.64–0.67 (m, 3H), 0.98–1.00 (m, 3H), 1.42–1.48 (m, 2H), 1.63–1.69 (m, 4H), 2.22–2.40 (m, 2H), 2.41–2.44 (m, 2H), 2.58–2.61 (m, 1H), 3.35–3.40 (m, 4H), 3.71 (s, 3H), 3.73 (m, 1H), 4.57–4.71 (brs, 1H), 6.53–6.61 (m, 2H), 6.77–6.80 (m, 1H), 7.13–7.15 (m, 3H), 7.26–7.28 (m, 2H), 7.93–7.95 (m, 1H), 8.68–8.92 (brs, 1H).

ESI-MS: 487.47 (MH$^+$).

Sweetening potency: 15000 times the sweetness of sugar.

Example 4

Synthesis of N-[3-(3-methoxy-4-hydroxyphenyl) propyl]-α-L-aspartyl N-(1R,2S,4S)-1-methyl-2-hydroxy-4-phenylhexyl amide (Table 1; Compound No.2)

An N-[3-(3-methoxy-4-hydroxyphenyl)propyl]-α-L-aspartyl N-(1R,2S,4S)-1-methyl-2-hydroxy-4-phenylhexyl amide was obtained as a solid material, with a total yield of 33.1%, in the same manner as in the Example 3, except using 3-(3-methoxy-4-benzyloxyphenyl)cinnamaldehyde in place of 3-(3-benzyloxy-4-methoxyphenyl) cinnamaldehyde.

$^1$HNMR (DMSO-d$_6$) δ: 0.64–0.67 (m, 3H), 0.98–1.00 (m, 3H), 1.43–1.50 (m, 2H), 1.67–1.73 (m, 4H), 2.22–2.36 (m, 2H), 2.38–2.48 (m, 2H), 2.59–2.63 (m, 1H), 3.38–3.42 (m, 4H), 3.70–3.72 (m, 1H), 3.73 (s, 3H), 4.53–4.71 (brs, 1H), 6.55–6.56 (m, 1H), 6.64–6.68 (m, 1H), 6.73 (s, 1H), 7.13–7.17 (m, 3H), 7.24–7.28 (m, 2H), 7.92–7.95 (m, 1H), 8.54–8.71 (brs, 1H).

ESI-MS: 487.47 (MH$^+$).

Sweetening potency: 10000 times the sweetness of sugar.

Example 5

Synthesis of N-[3-(2-hydroxy-4-methoxyphenyl) propyl]-α-L-aspartyl N-(1R,2S,4S)-1-methyl-2-hydroxy-4-phenylhexyl amide (Table 1; Compound No.3)

An N-[3-(2-hydroxy-4-methoxyphenyl)propyl]-α-L-aspartyl N-(1R,2S,4S)-1-methyl-2-hydroxy-4-phenylhexyl amide was obtained as a solid material, with a total yield of 32.3%, in the same manner as in the Example 3, except using 3-(2-benzyloxy-4-methoxyphenyl)cinnamaldehyde in place of 3-(3-benzyloxy-4-methoxyphenyl) cinnamaldehyde, and re-crystallizing the compound in the methanol-water.

$^1$HNMR (DMSO-d$_6$) δ: 0.64–0.68 (m, 3H), 0.98–1.00 (m, 3H), 1.42–1.50 (m, 2H), 1.62–1.73 (m, 4H), 2.22–2.41 (m, 2H), 2.43–2.47 (m, 2H), 2.58–2.62 (m, 1H), 3.36–3.43 (m, 4H), 3.65 (s, 3H), 3.70–3.75 (m, 1H), 4.58–4.69 (brs, 1H), 6.27–6.30 (m, 1H), 6.36–6.37 (m, 1H), 6.90–6.93 (m, 1H), 7.13–7.16 (m, 3H), 7.24–7.28 (m, 2H), 7.93–7.96 (m, 1H).
ESI-MS: 487.43 (MH$^+$).
Sweetening potency: 6000 times the sweetness of sugar.

Example 6

Synthesis of N-[3-(2,4-dihydroxyphenyl)propyl]-α-L-aspartyl N-(1R,2S,4S)-1-methyl-2-hydroxy-4-phenylhexyl amide (Table 1; Compound No.4)

An N-[3-(2,4-dihydroxyphenyl)propyl]-α-L-aspartyl N-(1R,2S,4S)-1-methyl-2-hydroxy-4-phenylhexyl amide was obtained as a solid material, with a total yield of 23.9%, in the same manner as in the Example 3, except using 3-(2,4-dibenzyloxyphenyl)cinnamaldehyde in place of 3-(3-benzyloxy-4-methoxyphenyl) cinnamaldehyde.

$^1$HNMR (DMSO-d$_6$) δ: 0.64–0.68 (m, 3H), 0.98–1.00 (m, 3H), 1.42–1.49 (m, 2H), 1.61–1.72 (m, 4H), 2.22–2.38 (m, 2H), 2.40–2.47 (m, 2H), 2.57–2.64 (m, 1H), 3.14–3.17 (m, 1H), 3.35–3.45 (m, 4H), 3.71–3.74 (m, 1H), 4.60–4.72 (brs, 1H), 6.10–6.12 (m, 1H), 6.25–6.26 (m, 1H), 6.76–6.79 (m, 1H), 7.14–7.16 (m, 3H), 7.24–7.28 (m, 2H), 7.96–7.98 (m, 1H), 8.90–8.11 (brs, 2H).
ESI-MS: 473.46 (MH$^+$).
Sweetening potency: 10000 times the sweetness of sugar.

Example 7

Synthesis of N-[3-(3-hydroxy-4-methylphenyl)propyl]-α-L-aspartyl N-(1R,2S,4S)-1-methyl-2-hydroxy-4-phenylhexyl amide (Table 1; Compound No.5)

An N-[3-(3-hydroxy-4-methylphenyl)propyl]-α-L-aspartyl N-(1R,2S,4S)-1-methyl-2-hydroxy-4-phenylhexyl amide was obtained as a solid material, with a total yield of 25.0%, in the same manner as in the Example 3, except using 3-(3-benzyloxy-4-methylphenyl) cinnamaldehyde in place of 3-(3-benzyloxy-4-methoxyphenyl) cinnamaldehyde, and re-crystallizing the compound in the methanol-water.

$^1$HNMR (DMSO-d$_6$) δ: 0.64–0.68 (m, 3H), 0.98–1.00 (m, 3H), 1.43–1.48 (m, 2H), 1.6–1.69 (m, 4H), 1.91 (s, 3H), 2.22–2.33 (m, 2H), 2.37–2.43 (m, 2H), 2.58–2.64 (m, 1H), 3.20–3.37 (m, 4H), 3.69–3.74 (m, 1H), 4.58–4.63 (brs, 1H), 6.49–6.51 (d, 1H), 6.59 (s, 1H), 6.91–6.93 (d, 1H), 7.13–7.17 (m, 3H), 7.24–7.28 (m, 2H), 7.88–7.90 (d, 1H), 9.03–9.10 (brs, 1H),
ESI-MS: 471.48 (MH$^+$).
Sweetening potency: 6000 times the sweetness of sugar.

Example 8

Synthesis of N-[3-(3-methyl-4-hydroxyphenyl)propyl]-α-L-aspartyl N-(1R,2S,4S)-1-methyl-2-hydroxy-4-phenylhexyl amide (Table 1; Compound No.6)

An N-[3-(3-methyl-4-hydroxyphenyl)propyl]-α-L-aspartyl N-(1R,2S,4S)-1-methyl-2-hydroxy-4-phenylhexyl amide was obtained as a solid material, with a total yield of 16.0%, in the same manner as in the Example 3, except using 3-(3-methyl-4-benzyloxyphenyl) cinnamaldehyde in place of the 3-(3-benzyloxy-4-methoxyphenyl) cinnamaldehyde.

$^1$HNMR (DMSO-d$_6$) δ: 0.64–0.68 (m, 3H), 0.98–1.00 (m, 3H), 1.43–1.50 (m, 2H), 1.62–1.71 (m, 4H), 2.14 (s, 3H), 2.24–2.34 (m, 2H), 2.37–2.46 (m, 2H), 2.59–2.64 (m, 1H), 3.24–3.41 (m, 4H), 3.68–3.72 (m, 1H), 4.58–4.63 (brs, 1H), 6.64–6.66 (m, 1H), 6.76–6.78 (m, 1H), 6.85 (s, 1H), 7.13–7.16 (m, 3H), 7.24–7.27 (m, 2H), 7.88–7.91 (m, 1H), 8.91–8.96 (brs, 1H).
ESI-MS: 471.48 (MH$^+$).
Sweetening potency: 4000 times the sweetness of sugar.

Example 9

Synthesis of N-[3-(4-hydroxyphenyl)propyl]-α-L-aspartyl N-(1R,2S,4S)-1-methyl-2-hydroxy-4-phenylhexyl amide (Table 1; Compound No.7)

An N-[3-(4-hydroxyphenyl)propyl]-α-L-aspartyl N-(1R,2S,4S)-1-methyl-2-hydroxy-4-phenylhexyl amide was obtained as a solid material, with a total yield of 16.0%, in the same manner as in the Example 3, except using 3-(4-benzyloxyphenyl) cinnamaldehyde in place of the 3-(3-benzyloxy-4-methoxyphenyl) cinnamaldehyde.

$^1$HNMR (DMSO-d$_6$) δ: 0.64–0.68 (m, 3H), 0.98–1.00 (m, 3H), 1.38–1.50 (m, 2H), 1.63–1.72 (m, 4H), 2.22–2.34 (m, 2H), 2.37–2.41 (m, 2H), 2.58–2.62 (m, 1H), 3.23–3.38 (m, 4H), 3.69–3.73 (m, 1H), 4.58–4.64 (brs, 1H), 6.64–6.66 (m, 2H), 6.95–6.97 (m, 2H), 7.14–7.16 (m, 3H), 7.24–7.28 (m, 2H), 7.88–7.91 (m, 1H), 9.05–9.10 (brs, 1H).
ESI-MS: 457.36 (MH$^+$).
Sweetening potency: 6000 times the sweetness of sugar.

Example 10

Synthesis of N-[3-(4-methoxyphenyl)propyl]-α-L-aspartyl N-(1R,2S,4S)-1-methyl-2-hydroxy-4-phenylhexyl amide (Table 1; Compound No.8)

An N-[3-(4-methoxyphenyl)propyl]-α-L-aspartyl N-(1R,2S,4S)-1-methyl-2-hydroxy-4-phenylhexyl amide was obtained as a solid material, with a total yield of 34.9%, in the same manner as in the Example 3, except using 3-(4-methoxyphenyl) cinnamaldehyde in place of the 3-(3-benzyloxy-4-methoxyphenyl) cinnamaldehyde.

$^1$HNMR (DMSO-d$_6$) δ: 0.64–0.68 (m, 3H), 0.93–1.00 (m, 3H), 1.44–1.51 (m, 2H), 1.62–1.71 (m, 4H), 2.23–2.36 (m, 2H), 2.38–2.46 (m, 2H), 2.58–2.63 (m, 2H), 3.34–3.38 (m, 4H), 3.71 (s, 3H), 3.72–3.75 (m, 1H), 4.59–4.64 (brs, 1H), 6.81–6.83 (m, 2H), 7.08–7.10 (m, 2H), 7.13–7.16 (m, 3H), 7.24–7.28 (m, 2H), 7.89–7.91 (m, 1H).
ESI-MS: 471.48 (MH$^+$).
Sweetening potency: 3000 times the sweetness of sugar.

Example 11

Synthesis of N-[3-methyl-3-(3-hydroxy-4-methoxyphenyl) butyl]-α-L-aspartyl N-(1R,2S,4S)-1-methyl-2-hydroxy-4-phenylhexyl amide (Table 1; Compound No.9)

An N-[3-methyl-3-(3-hydroxy-4-methoxyphenyl)butyl]-α-L-aspartyl N-(1R,2S,4S)-1-methyl -2-hydroxy-4-phenylhexyl amide was obtained as a solid material, with a total yield of 53.0%, in the same manner as in the Example 3, except using 3-methyl-3-(3-benzyloxy-4-methoxyphenyl) butylaldehyde in place of the 3-(3-benzyloxy-4-methoxyphenyl) cinnamaldehyde.

$^1$HNMR (DMSO-d$_6$) δ: 0.64–0.68 (m, 3H), 0.95–0.97 (m, 3H), 1.16 (s, 6H), 1.41–1.48 (m, 2H), 1.64–1.80 (m, 4H), 2.08–2.34 (m, 4H), 2.58–2.62 (m, 1H), 3.30–3.37 (m, 2H), 3.71 (s, 3H), 4.58–4.64 (brs, 1H), 6.63–6.65 (m, 1H), 6.75–6.79 (m, 2H), 7.14–7.18 (m, 3H), 7.25–7.28 (m, 2H), 7.86–7.88 (m, 1H), 8.68–8.81 (brs, 1H).

ESI-MS: 515.51 (MH$^+$).

Sweetening potency: 15000 times the sweetness of sugar.

Example 12

Synthesis of N-[3-methyl-3-(3-methyl-4-hydroxyphenyl)butyl]-α-L-aspartyl N-(1R,2S,4S)-1-methyl-2-hydroxy-4-phenylhexyl amide (Table 1; Compound No.10)

An N-[3-methyl-3-(3-methyl-4-hydroxyphenyl)butyl]-α-L-aspartyl N-(1R,2S,4S)-1-methyl -2-hydroxy-4-phenylhexyl amide was obtained as a solid material, with a total yield of 25.4%, in the same manner as in the Example 3, except using 3-methyl-3-(3-methyl-4-benzyloxyphenyl) butylaldehyde in place of the 3-(3-benzyloxy-4-methoxyphenyl) cinnamaldehyde.

$^1$HNMR (DMSO-d$_6$) δ: 0.64–0.68 (m, 3H), 0.95–0.97 (m, 3H), 1.17 (s, 6H), 1.43–1.49 (m, 2H), 1.67–1.73 (m, 4H), 2.09 (s, 3H), 2.13–2.34 (m, 4H), 2.58–2.63 (m, 1H), 3.32–3.35 (m, 2H), 3.66–3.70 (m, 1H), 4.57–4.63 (brs, 1H), 6.66–6.68 (m, 1H), 6.88–6.90 (m, 1H), 6.97 (s, 1H), 7.14–7.18 (m, 3H), 7.24–7.28 (m, 2H), 7.84–7.87 (m, 1H), 8.86–8.92 (brs, 1H).

ESI-MS: 499.43 (MH$^+$).

Sweetening potency: 15000 times the sweetness of sugar.

Example 13

Synthesis of N-[3-(3-hydroxy-4-methoxyphenyl) propyl]-α-L-aspartyl N-(1R,2S,4R)-1-methyl-2-hydroxy-4-phenylhexyl amide (Table 1; Compound No.11)

An N-[3-(3-hydroxy-4-methoxyphenyl)propyl]-α-L-aspartyl N-(1R,2S,4R)-1-methyl-2-hydroxy-4-phenylhexyl amide was obtained as a solid material, with a total yield of 32.9%, in the same manner as in the Example 3, except using N-t-butoxycarbonyl-β-O-benzyl-α-L-aspartyl N-(1R,2S,4R)-1-methyl-2-hydroxy-4-phenylhexyl amide in place of the N-t-butoxycarbonyl-β-O-benzyl-α-L-aspartyl N-(1R,2S,4S)-1-methyl-2-hydroxy-4-phenylhexyl amide.

$^1$HNMR (DMSO-d$_6$) δ: 0.67–0.70 (m, 3H), 0.91–0.93 (m, 3H), 1.47–1.62 (m, 4H), 1.64–1.68 (m, 2H), 2.22–2.37 (m, 2H), 2.43–2.46 (m, 2H), 2.64–2.70 (m, 1H), 2.90–2.95 (m, 1H), 3.37–3.39 (m, 2H), 3.55–3.58 (m, 1H), 3.72 (s, 3H), 4.56–4.61 (brs, 1H), 6.53–6.55 (m, 1H), 6.61 (s, 1H), 6.74–6.80 (m, 1H), 7.14–7.17 (m, 3H), 7.24–7.28 (m, 2H), 7.82–7.84 (m, 1H), 8.78–8.83 (brs, 1H).

ESI-MS: 487.43 (MH$^+$).

Sweetening potency: 4000 times the sweetness of sugar.

Example 14

Synthesis of N-[3-(3-hydroxy-4-methoxyphenyl) propyl]-α-L-aspartyl N-(1R,2RS)-1-methyl-2-hydroxy-3-cyclohexylpropyl amide (Table 1; Compound No.12)

An N-[3-(3-hydroxy-4-methoxyphenyl)propyl]-α-L-aspartyl N-(1R,2RS)-1-methyl-2-hydroxy-3-cyclohexylpropyl amide was obtained as a solid material, with a total yield of 23.3%, in the same manner as in the Example 3, except using N-t-butoxycarbonyl-β-O-benzyl-α-L-aspartyl N-(1R,2RS)-1-methyl-2-hydroxy-3-cyclohexylpropyl amide in place of the N-t-butoxycarbonyl-β-O-benzyl-α-L-aspartyl N-(1R,2S,4S)-1-methyl-2-hydroxy-4-phenylhexyl amide.

$^1$HNMR (DMSO-d$_6$) δ: 0.75–0.77 (m, 1H), 0.86–0.88 (m, 1H), 0.96–1.00 (m, 3H), 1.01–1.19 (m, 5H), 1.36–1.41 (m, 1H), 1.59–1.66 (m, 7H), 2.23–2.37 (m, 2H), 2.40–2.45 (m, 2H), 3.43–3.49 (m, 3H), 3.58–3.62 (m, 1H), 3.74 (s, 3H), 3.75–3.78 (m, 1H), 4.61–4.66 (brs, 1H), 6.53–6.55 (m, 1H), 6.61 (s, 1H), 6.77–6.80 (m, 1H), 7.81–7.83 (d, 0.7H), 7.92–7.94 (d, 0.3H), 8.76–8.81 (brs, 1H).

ESI-MS: 451.44 (MH$^+$).

Sweetening potency: 4000 times the sweetness of sugar.

Example 15

Synthesis of N-[3-(3-hydroxy-4-methoxyphenyl) propyl]-α-L-aspartyl N-(1R,2R)-1-methyl-2-hydroxy-3-cyclohexylpropyl amide (Table 1; Compound No.13)

A (1R,2R)-N-t-butoxycarbonyl-1-methyl-2-hydroxy-3-cyclohexylpropyl amine was synthesized according to the method of M. T. Reetz et al, and purified through PTLC whereby the stereoisomer (optical isomer) thereof was removed (refer to M. T. Reetz, et. al., Tetrahedron: Asymmetry vol.1, pp. 375–378, 1990).

An N-[3-(3-hydroxy-4-methoxyphenyl)propyl]-α-L-aspartyl N-(1R,2R)-1-methyl-2-hydroxy-3-cyclohexylpropyl amide was obtained as a solid material, with a total yield of 65.5%, in the same manner as in the Example 3, except using N-t-butoxycarbonyl-β-O-benzyl-α-L-aspartyl N-(1R,2R)-1-methyl-2-hydroxy-3-cyclohexylpropyl amide in place of the N-t-butoxycarbonyl-β-O-benzyl-α-L-aspartyl N-(1R,2S,4S)-1-methyl-2-hydroxy-4-phenylhexyl amide.

$^1$HNMR (DMSO-d$_6$) δ: 0.79–0.81 (m, 1H), 0.84–0.93 (m, 1H), 1.00–1.02 (d, 2H), 1.06–1.27 (m, 6H), 1.32–1.44 (brs, 1H), 1.53–1.69 (m, 5H), 1.72–1.84 (m, 1H), 2.45–2.50 (m, 2H), 2.61–2.63 (d, 2H), 2.64–2.71 (m, 2H), 3.46–3.54 (m, 1H), 3.72 (s, 3H), 3.74–3.79 (m, 1H), 3.83–3.88 (m, 1H), 4.66–4.72 (brs, 1H), 6.53–6.55 (m, 1H), 6.61 (s, 1H), 6.79–6.81 (m, 1H), 8.12–8.14 (d, 1H), 8.79–8.90 (brs, 1H).

ESI-MS: 451.44 (MH$^+$).

Sweetening potency: 5000 times the sweetness of sugar.

Example 16

Synthesis of N-[3-methyl-3-(3-hydroxy-4-methoxyphenyl)butyl]-α-L-aspartyl N-(1R,2R)-1-methyl-2-hydroxy-3-cyclohexylpropyl amide (Table 1; Compound No.14)

An N-[3-methyl-3-(3-hydroxy-4-methoxyphenyl)butyl]-α-L-aspartyl N-(1R,2R)-1-methyl-2-hydroxy-3-cyclohexylpropyl amide was obtained as a solid material, with a total yield of 48.4%, in the same manner as in the Example 3, except using N-t-butoxycarbonyl-β-O-benzyl-α-L-aspartyl N-(1R,2R)-1-methyl-2-hydroxy-3-cyclohexylpropyl amide in place of the N-t-butoxycarbonyl-β-O-benzyl-α-L-aspartyl N-(1R,2S,4S)-1-methyl-2-hydroxy-4-phenylhexyl amide, and using 3-methyl-3-(3-hydroxy-4-methoxyphenyl) butylaldehyde in place of the 3-(3-benzyloxy-4-methoxyphenyl) cinnamaldehyde.

$^1$HNMR (DMSO-d$_6$) δ: 0.60–0.80 (m, 1H), 0.83–0.92 (m, 1H), 0.98–1.00 (d, 3H), 1.02–1.16 (m, 4H), 1.19 (s, 6H), 1.33–1.46 (brs, 1H), 1.57–1.71 (m, 6H), 1.73–1.94 (m, 2H), 2.41–2.48 (m, 2H), 2.53–2.58 (m, 2H), 3.31–3.35 (m, 1H), 3.43–3.51 (m, 1H), 3.73 (s, 3H), 3.76–3.82 (m, 1H), 4.63–4.74 (brs, 1H), 6.63–6.67 (m, 1H), 6.75 (s, 1H), 6.80–6.82 (m, 1H), 7.99–8.04 (d, 1H), 8.72–8.87 (brs, 1H).
ESI-MS: 479.32 (MH$^+$).
Sweetening potency: 5000 times the sweetness of sugar.

Example 17

Synthesis of N-(3,3-dimethyl-5-hydroxypentyl)-α-L-aspartyl N-(1R,2S,4S)-1-methyl-2-hydroxy-4-phenylhexyl amide (Table 1; Compound No.15)

An N-(3,3-dimethyl-5-hydroxypentyl)-α-L-aspartyl N-(1R,2S,4S)-1-methyl-2-hydroxy-4-phenylhexyl amide was obtained as a solid material, with a total yield of 44.2%, in the same manner as in the Example 3, except using 3,3-dimethyl-5-t-butyldimethylsilyloxypentylaldehyde in place of the 3-(3-benzyloxy-4-methoxyphenyl) cinnamaldehyde and conducting a process for removing the t-butyldimethylsilyl group with 1N—HCl in methanol before the catalytic reduction.
$^1$HNMR (DMSO-d$_6$) δ: 0.64–0.68 (m, 3H), 0.82 (s, 6H), 0.99–1.01 (m, 3H), 1.32–1.41 (m, 4H), 1.45–1.51 (m, 2H), 1.67–1.72 (m, 2H), 2.14–2.24 (m, 1H), 2.34–2.39 (m, 1), 2.45–2.48 (m, 2H), 2.59–2.62 (m, 1H), 3.36–3.44 (m, 4H), 3.72–3.75 (m, 1H), 4.60–4.70 (brs, 1H), 7.15–7.17 (m, 3H), 7.24–7.28 (m, 2H), 7.94–7.96 (m, 1H).
ESI-MS: 437.55 (MH$^+$).
Sweetening potency: 6500 times the sweetness of sugar.

Example 18

Synthesis of N-(3,3-dimethyl-6-hydroxyhexyl)-α-L-aspartyl N-(1R,2S,4S)-1-methyl-2-hydroxy-4-phenylhexyl amide (Table 1; Compound No.16)

An N-(3,3-dimethyl-6-hydroxyhexyl)-α-L-aspartyl N-(1R,2S,4S)-1-methyl-2-hydroxy-4-phenylhexyl amide was obtained as a solid material, with a total yield of 44.2%, in the same manner as in the Example 3, except using 3,3-dimethyl-6-benzyloxyhexylaldehyde in place of the 3-(3-benzyloxy-4-methoxyphenyl) cinnamaldehyde.
$^1$HNMR (DMSO-d$_6$) δ: 0.64–0.68 (t, 3H), 0.80 (s, 6H), 0.99–1.00 (m, 3H), 1.09–1.14 (m, 2H), 1.33–1.36 (m, 4H), 1.44–1.51 (m, 2H), 1.66–1.72 (m, 2H), 2.18–2.23 (m, 1H), 2.25–2.35 (m, 1H), 2.38–2.50 (m, 2H), 2.55–2.62 (m, 1H), 3.32–3.39 (m, 3H), 3.43–3.45 (m, 3.72–3.75 (m, 1H), 7.15–7.17 (m, 3H), 7.24–7.28 (m, 2H), 8.02–8.04 (m, 1H).
ESI-MS: 451.44 (MH$^+$).
Sweetening potency: 4500 times the sweetness of sugar.

Example 19

Table 1 shows the structures and the results of the sensory tests on the several synthesized N-alkyl aspartyl amide derivatives, represented by the following general formula (5), the synthesis of which, as well as the results are presented above in Examples 3–18.

As may be seen from the results of the Table 1, the novel derivatives of the present invention are particularly excellent in degree of sweetness (sweetening potency).

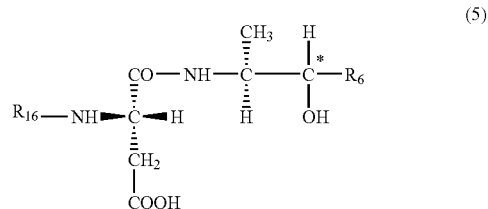

(5)

In the above formula (5), R$_6$ and C* have the same meanings or definitions as the R$_6$ and C* used in the foregoing formula (1), and the explanations for the R$_6$ and C* described there are also applied thereto. R$_{16}$ means any one of the substituent groups shown in the following Table 1.

TABLE 1

Structure of N-alkyl aspartyl amide derivative and Sweetening potency:

| Compound Sweetening No. | R$_{16}$[1] | C*Configuration (S:R) | R$_6$[2] | Potency[3] |
|---|---|---|---|---|
| 1 | 3-(3-OH-4-OMe—Ph)propyl | >5:1 | (S)-2-phenylbutyl | 15000 |
| 2 | 3-(3-OMe-4-OH—Ph)propyl | >5:1 | (S)-2-phenylbutyl | 10000 |
| 3 | 3-(2-OH-4-OMe—Ph)propyl | >5:1 | (S)-2-phenylbutyl | 6000 |
| 4 | 3-(2,4-di.OH—Ph)propyl | >5:1 | (S)-2-phenylbutyl | 10000 |
| 5 | 3-(3-OH-4-Me—Ph)propyl | >5:1 | (S)-2-phenylbutyl | 6000 |
| 6 | 3-(3-Me-4-OH—Ph}propyl | >5:1 | (S)-2-phenylbutyl | 4000 |
| 7 | 3-(4-OH—Ph)propyl | >5:1 | (S)-2-phenylbutyl | 6000 |
| 8 | 3-(4-OMe—Ph)propyl | >5:1 | (S)-2-phenylbutyl | 3000 |
| 9 | 3-Me-3-(3-OH-4-OMe—Ph)butyl | >5:1 | (S)-2-phenylbutyl | 15000 |
| 10 | 3-Me-3-(3-Me-4-OH—Ph)butyl | >5:1 | (S)-2-phenylbutyl | 15000 |
| 11 | 3-(3-OH-4-OMe—Ph)propyl | >9:1 | (R)-2-phenylbutyl | 4000 |
| 12 | 3-(3-OH-4-OMe—Ph)propyl | 3:7 | cyclohexylmethyl | 4000 |
| 13 | 3-(3-OH-4-OMe—Ph)propyl | 1:>9 | cyclohexylmethyl | 5000 |
| 14 | 3-Me-3-(3-OH-4-OMe—Ph)butyl | 1:>9 | cyclohexylmethyl | 5000 |
| 15 | 3,3-di.Me-5-OH-pentyl | >5:1 | (S)-2-phenylbutyl | 6500 |
| 16 | 3,3-di.Me-6-OH-hexyl | >5:1 | (S)-2-phenylbutyl | 4500 |

[1]OH: hydroxy, OMe: methoxy, Me: methyl, Ph: phenyl, di-OH: dihydroxy, di-Me: dimethyl;
[2]steric configuration (R or S) defined based on the structure in the form wherein R$_6$ is bonded to C* carbon; and
[3]values compared to sweetening potency of a 4% aqueous solution of sucrose.

Incidentally, in the description of the present application or the above Table, ">5" dentoes a numerical value of more than 5, and ">9" denotes a numerical value of more than 9, respectively. And, in the above Table, regarding the steric configuration of the 2-phenylbutyl group, the configuration is shown when the group is observed in the molecule on the whole. Therefore, the (S) configuration as shown there means a (S) configuration when the 2-phenylbutyl group is observed in the molecule on the whole, and on the other hand, it means a (R) configuration when the substituent group as such only is watched and observed.

Based on the foregoing, the present invention provides a safe, low-calorie sweetening agent possessing a superior sweetening potency compared with conventional sweetening agents. In addition, the present invention provides a sweetened food, a sweetened drink, and a similar sweetened product using the low-calorie sweetening agent of the present invention.

In addition, a novel N-alkylaspartyl amide derivative, including the salt form thereof, such as N-[3-(3-hydroxy-4-methoxyphenyl)propyl]-α-L-aspartyl N-(1R,2S,4S)-1-methyl-2-hydroxy-4-phenylhexyl amide, is provide, which is an excellent, effective ingredient of the inventive sweetening agent.

The novel derivative provided by the present invention possesses an improved solubility in water and an improved stability. Accordingly, it is now possible to expect a further improvement in processing characteristics and enlargement of use application therefor.

Numerous modifications and variations on the present invention are possible in light of the above teachings. It is, therefore, to be understood that within the scope of the accompanying claims, the invention may be practiced otherwise than as specifically described herein.

What is claimed is:
1. An N-alkylaspartyl amide compound represented by the following formula (1):

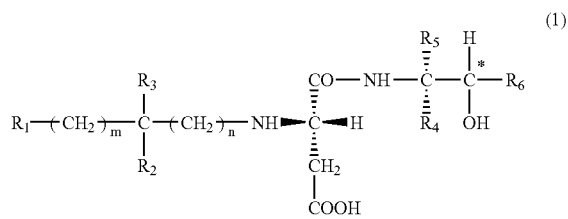

wherein:
$R_1$ is selected from the group consisting of a hydroxyl group, an alkoxy group having 1 to 4 carbon atoms, an alkoxycarbonyl group having 2 to 5 carbon atoms, and a substituent group represented by the following general formula (2), and

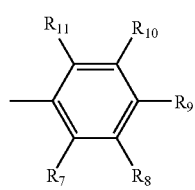

wherein $R_7$, $R_8$, $R_9$, $R_{10}$ and $R_{11}$ are reciprocally independent from each other and each denotes a substituent group selected from the group consisting of a hydrogen atom, a hydroxyl group, an alkoxy group having 1 to 3 carbon atoms and an alkyl group having 1 to 3 carbon atoms, or wherein $R_7$ and $R_8$, or $R_8$ and $R_9$ may be combined together to form a methylene dioxy group, provided that at least one of $R_7$, $R_8$, $R_9$, $R_{10}$ and $R_{11}$ is not a hydrogen atom;

$R_2$ and $R_3$ are reciprocally independent from each other and each denotes a substituent group selected from the group consisting of a hydrogen atom and an alkyl group having 1 to 4 carbon atoms, or wherein $R_2$ and $R_3$ are combined together to form an alkylene group having 2 to 5 carbon atoms;

m and n are reciprocally independent from each other and each represents a numerical value selected from 0, 1, 2, 3 and 4;

$R_4$ and $R_5$ are reciprocally independent from each other and each denotes a substituent group selected from the group consisting of a hydrogen atom, an alkyl group having 1 to 6 carbon atoms, an alkoxyalkyl group having 2 to 7 carbon atoms, a hydroxyalkyl group having 1 to 6 carbon atoms, a phenyl group, and a 2-furyl group, or wherein $R_4$ and $R_5$ are combined together to form an alkylene group having 2 to 5 carbon atoms;

$R_6$ is selected from the group consisting of an alkyl group having 1 to 12 carbon atoms, a substituent group represented by the following formula (3), and a substituent group represented by the following formula (4)

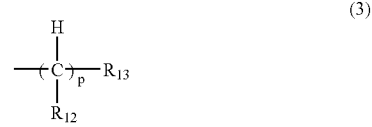

wherein $R_{12}$ represents a substituent group selected from the group consisting of a hydrogen atom and an alkyl group having 1 to 4 carbon atoms; $R_{13}$ represents a carbocyclic compound residue group which contains 3 to 12-membered ring(s), wherein the 3 to 12-membered ring(s) are substituted or unsubstituted, and wherein the 3 to 12-membered ring(s) are saturated or unsaturated; and p denotes 0 or 1,

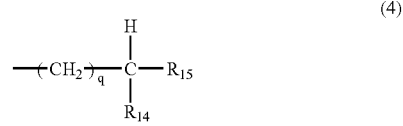

wherein $R_{14}$ and $R_{15}$ are reciprocally independent from each other and each denotes a substituent group selected from the group consisting of a phenyl group, a hydrogen atom, a cycloalkyl group having 3 to 4 carbon atoms, an alkyl group having 1 to 6 carbon atoms, an alkoxyalkyl group having 2 to 7 carbon atoms and a 2-or 3-thienyl group, wherein said phenyl group may have a substituent group(s) selected from the group consisting of hydroxyl group(s), alkoxy group(s) having 1 to 3 carbon atoms, alkyl group(s)

having 1 to 3 carbon atoms and methylene dioxy group(s); and q denotes 0 or 1; and C* means an any steric configuration; or a salt form thereof.

2. The N-alkylaspartyl amide compound of claim 1, wherein
$R_1$ is selected from the group consisting of a hydroxyl group, a 3-hydroxy-4-methoxyphenyl group, a 3-methoxy-4-hydroxyphenyl group, a 2-hydroxy-4-methoxyphenyl group, a 2,4-dihydroxyphenyl group, a 3-hydroxy-4-methylphenyl group, a 3-methyl-4-hydroxyphenyl group, a 4-hydroxyphenyl group, a 4-methoxyphenyl group and a 3-methyl-4-hydroxyphenyl group;
$R_2$ is a hydrogen atom or a methyl group;
$R_3$ is a hydrogen atom or a methyl group;
$R_4$ is a hydrogen atom;
$R_5$ is a methyl group;
$R_6$ is a 2-phenylbutyl group or a cyclohexylmethyl group;
m is 0 or any one of the integers from 1 to 3; and
n is 0, 1 or 2.

3. The N-alkylaspartyl amide compound of claim 1, wherein the steric configuration of C* is selected from the group consisting of a (R) form, a (S) form, and a (RS) form.

4. The N-alkylaspartyl amide compound of claim 1, wherein $R_6$ is selected from the group consisting of a (R)-substituent group, a (S)-substituent group, and a (RS)-substituent group.

5. The N-alkylaspartyl amide compound of claim 1, wherein $R_1$ is a 3-hydroxy-4-methoxyphenyl group; $R_2$, $R_3$ and $R_4$ are a hydrogen atom; $R_5$ is a methyl group; $R_6$ is a 2-phenylbutyl group; and m and n are 1.

6. The N-alkylaspartyl amide compound of claim 1, wherein $R_1$ is a 3-methoxy-4-hydroxyphenyl group; $R_2$, $R_3$ and $R_4$ are a hydrogen atom; $R_5$ is a methyl group; $R_6$ is a 2-phenylbutyl group; and m and n are 1.

7. The N-alkylaspartyl amide compound of claim 1, wherein $R_1$ is a 2-hydroxy-4-methoxyphenyl group; $R_2$, $R_3$ and $R_4$ are a hydrogen atom; $R_5$ is a methyl group; $R_6$ is a 2-phenylbutyl group; and m and n are 1.

8. The N-alkylaspartyl amide compound of claim 1, wherein $R_1$ is a 2,4-dihydroxyphenyl group; R2, $R_3$ and $R_4$ are a hydrogen atom; $R_5$ is a methyl group; $R_6$ is a 2-phenylbutyl group; and m and n are 1.

9. The N-alkylaspartyl amide compound of claim 1, wherein $R_1$ is a 3-hydroxy-4-methylphenyl group; $R_2$, $R_3$ and $R_4$ are a hydrogen atom; $R_5$ is a methyl group; $R_6$ is a 2-phenylbutyl group; and m and n are 1.

10. The N-alkylaspartyl amide compound of claim 1, wherein $R_1$ is a 3-methyl-4-hydroxyphenyl group; $R_2$, $R_3$ and $R_4$ are a hydrogen atom; $R_5$ is a methyl group; $R_6$ is a 2-phenylbutyl group; and m and n are 1.

11. The N-alkylaspartyl amide compound of claim 1, wherein $R_1$ is a 4-hydroxyphenyl group; $R_2$, $R_3$ and $R_4$ are a hydrogen atom; $R_5$ is a methyl group; $R_6$ is a 2-phenylbutyl group; and m and n are 1.

12. The N-alkylaspartyl amide compound of claim 1, wherein $R_1$ is a 4-methoxyphenyl group; $R_2$, $R_3$ and $R_4$ are a hydrogen atom; $R_5$ is a methyl group; $R_6$ is a 2-phenylbutyl group; and m and n are 1.

13. The N-alkylaspartyl amide compound of claim 1, wherein $R_1$ is a 3-hydroxy-4-methoxyphenyl group; $R_2$, $R_3$ and $R_5$ are a methyl group; $R_4$ is a hydrogen atom; $R_6$ is a 2-phenylbutyl group; m is 0, and n is 2.

14. The N-alkylaspartyl amide compound of claim 1, wherein $R_1$ is a 3-methyl-4-hydroxyphenyl group; $R_2$, $R_3$ and $R_5$ are a methyl group; $R_4$ is a hydrogen atom; $R_6$ is a 2-phenylbutyl group; m is 0, and n is 2.

15. The N-alkylaspartyl amide compound of claim 1, wherein $R_1$ is a 3-hydroxy-4-methoxyphenyl group; $R_2$, $R_3$ and $R_4$ are a hydrogen atom; $R_5$ is a methyl group; $R_6$ is a cyclohexylmethyl group; and m and n are 1.

16. The N-alkylaspartyl amide compound of claim 1, wherein $R_1$ is a 3-hydroxy-4-methoxyphenyl group; $R_2$, $R_3$ and $R_5$ are a methyl group; $R_4$ is a hydrogen atom; $R_6$ is a cyclohexylmethyl group; m is 0; and n is 2.

17. The N-alkylaspartyl amide compound of claim 1, wherein $R_1$ is a hydroxyl group; $R_2$, $R_3$ and $R_5$ are a methyl group; $R_4$ is a hydrogen atom; $R_6$ is a 2-phenylbutyl group; and m and n are 2.

18. The N-alkylaspartyl amide compound of claim 1, wherein $R_1$ is a hydroxyl group; $R_2$, $R_3$ and $R_5$ are a methyl group; $R_4$ is a hydrogen atom; $R_6$ is a 2-phenylbutyl group; m is 3; and n is 2.

19. The N-alkylaspartyl amide compound of claim 1, wherein said salt form is a salt selected from the group consisting of a salt with an alkali metal, a salt with an alkali earth metal, an ammonium salt, a salt with an amino acid, a salt with an inorganic acid, and a salt with an organic acid.

20. The N-alkylaspartyl amide compound of claim 1, wherein said salt form is a salt with at least one substance of another sweetener ingredient selected from the group consisting of saccharin, acesulfame, cyclamic acid and glycyrrhizic acid.

21. A sweetening agent comprising one or more N-alkylaspartyl amide compounds of claim 1 as an effective ingredient.

22. The sweetening agent of claim 21, further comprising one or more carriers or bulking agents.

23. A food or drink product comprising one or more N-alkylaspartyl amide compounds of claim 1 as an effective ingredient.

24. The food or drink product of claim 21, further comprising one or more carriers or bulking agents.

* * * * *